(12) United States Patent
Jin et al.

(10) Patent No.: US 7,579,003 B2
(45) Date of Patent: Aug. 25, 2009

(54) HBSAG-BCG COMBINED VACCINE FOR INTRACUTANEOUS INJECTION AND PREPARATION METHOD THEREOF

(75) Inventors: Lijie Jin, Changchun (CN); Zhi Wang, Changchun (CN); Xiaolin Zhao, Changchun (CN); Lihua Yang, Changchun (CN); Wange Chen, Changchun (CN); Aidong Yu, Changchun (CN); Junye Sun, Changchun (CN); Fuxue Zou, Changchun (CN); Yanming Liu, Changchun (CN); Aihong Liu, Changchun (CN); Lihong Yu, Changchun (CN); Yan Cai, Changchun (CN); Manlun Yu, Changchun (CN); Yuwu Wang, Changchun (CN); Changjun Zhou, Changchun (CN); Tong Yang, Changchun (CN); Dejuan Li, Changchun (CN); Xuan Luo, Changchun (CN); Li Li, Changchun (CN)

(73) Assignee: Changchun Institute of Biological Products, Jihn Province (CN)

( * ) Notice: Subject to any disclaimer, the term of this patent is extended or adjusted under 35 U.S.C. 154(b) by 274 days.

(21) Appl. No.: 10/559,471

(22) PCT Filed: May 26, 2004

(86) PCT No.: PCT/CN2004/000534

§ 371 (c)(1),
(2), (4) Date: May 22, 2006

(87) PCT Pub. No.: WO2004/108156

PCT Pub. Date: Dec. 16, 2004

(65) Prior Publication Data

US 2006/0257423 A1    Nov. 16, 2006

(30) Foreign Application Priority Data

Jun. 6, 2003  (CN) .............................. 03 1 27065

(51) Int. Cl.
*A61A 39/00* (2006.01)
*A61K 39/29* (2006.01)
*A61K 38/00* (2006.01)
*A61K 39/04* (2006.01)

(52) U.S. Cl. .............. 424/184.1; 424/189.1; 424/225.1; 424/248.1; 530/350

(58) Field of Classification Search ................ None
See application file for complete search history.

(56) References Cited

U.S. PATENT DOCUMENTS 4,710,378 A * 12/1987 Ohtomo et al. .......... 424/227.1

FOREIGN PATENT DOCUMENTS

| WO | WO 97/29773 | 8/1997 |
| WO | WO 97/33614 | 9/1997 |
| WO | WO 01/34801 A2 | 5/2001 |

OTHER PUBLICATIONS

Tain X-E et al. "The interation of hepatitis B vaccine and BCG in simultaneous asministration" Henan Medical Research vol. 4, No. 2, 127-132, 1995, Cited in IDS.*
Xiao-En, T. et al. (1995) "The interaction of Hepatitis B Vaccine and BCG in Simultaneous Administration" Henan Medical Research 4:127-132 (Chinese version).
Ota, M.O.C. et al. (2002) "Influence of *Mycobacterium bovis* Bacillus Calmette-Guerin on Antibody and Cytokine Responses to Human Neonatal Vaccination" The Journal of Immunology 168:919-925.
International Search Report from PCT priority application No. PCT/CN2004/000534, Aug. 12, 2004.

* cited by examiner

*Primary Examiner*—Bo Peng
(74) *Attorney, Agent, or Firm*—Knobbe Martens Olson & Bear LLP

(57) ABSTRACT

The present invention provides a combined vaccine that includes hepatitis B vaccine (HeVac) and Bacille Calmette-Guerin (BCG) for intracutaneous injection and the method of preparation of such vaccine. The combined vaccine changes the now used liquid agent of the HeVac into a cryoprotectant, thus improving the heat stability of the HBsAg. Because of the cryoprotectant in the combined vaccine, the heat stability of the HBsAg is improved, and the efficacy of the vaccine is only slightly decreased after 30 days at 37° C., and the decrease is lower than with the liquid agent of the HeVac. The present invention changes the newborn's inoculation from two injections into one to simultaneously obtain prophylaxis of hepatitis B and tuberculosis.

3 Claims, No Drawings

HBSAG-BCG COMBINED VACCINE FOR INTRACUTANEOUS INJECTION AND PREPARATION METHOD THEREOF

RELATED APPLICATIONS

This application is a U.S. National Phase of International Application No.: PCT/CN2004/000534, filed May 26, 2004, designating the U.S. and not published in English as WO 2004/108156 on Dec. 16, 2004, claiming the benefit of priority of Chinese Patent Application No.: 03127065.4, filed Jun. 6, 2003.

FIELD OF THE INVENTION

The present invention relates to the preparation of vaccine, and more particularly to a HBsAg(Hepatitis B virus surface Antigen)-BCG(Bacille Calmette-Guérin) combined vaccine for intracutaneous injection, the formulation of HBsAg-BCG combined vaccine and a freeze drying process for its preparation. In addition, the present invention provides a cryoprotective agent useful for the HBsAg-BCG combined vaccine, and the dosage and pathway of inoculation of the HBsAg-BCG combined vaccine.

BACKGROUND OF THE INVENTION

Hepatitis B (HB) and Tuberculosis are infectious diseases and can be efficiently prevented by inoculation of corresponding vaccines, respectively. According to the requirements of Immunization Project, neonate is obligatory to be inoculated with both HB and BCG vaccines within twenty-four hours after birth. Currently, BCG vaccine is provided in a lyophilized form and intracutaneously inoculated into the deltoid muscle of the upper arm, while HB vaccine for intracutaneous injection is provided in a liquid form and intramuscularly inoculated into the deltoid muscle of the upper arm, wherein the HB vaccine comprises aluminium adjuvant and a preservative. Both the BCG vaccine and HB vaccine are univalent vaccine and are required to be used separately for inoculation at a same day. Because the difference between the BCG and HB vaccines in inoculation pathway and the presence of preservative in HB vaccine currently used, BCG and HB vaccines can not be simply mixed together for inoculation. Therefore, the inoculations of BCG and HB vaccines require two injections, which is painful for neonate and incur much inconvenience. The objective of the present invention is to accomplish the inoculation of BCG and HB vaccines by one injection.

DETAILED DESCRIPTION OF THE INVENTION

The present invention provides an HBsAg (Hepatitis B virus surface Antigen)-BCG (Bacille Calmette-Guérin) combined vaccine for intracutaneous injection, which reduces previous two injections for neonate to one injection while retaining the prevention effect for HB and Tuberculosis.

The present invention also provides an HBsAg-BCG combined vaccine for intracutaneous injection, which is in a lyophilized form.

The present invention further provides a method for the preparation of the HBsAg-BCG combined vaccine and the method is applicable to industrial production.

The Hepatitis B and BCG combined vaccine for intracutaneous injection is provided in 0.2 ml vials, each comprising the following components:

| | |
|---|---|
| HBsAg | 5 µg~20 µg |
| BCG | 80 µg~120 µg |
| Gelatin | 0.8~1.2 mg |
| Saccharose | 8~12 mg |
| KCl | 0.8~1.2 mg |
| Sodium glutamate | 0.8~1.2 mg |
| NaCl | 0.8~0.9 mg |
| pH | 6.0~7.5 |

The method for the preparation of HBsAg-BCG combined vaccine according to the present invention includes the following steps:

(1) Providing a stock solution of BCG, wherein 1 mL stock solution of BCG is consisted of the following components:

| | |
|---|---|
| BCG | 800~1200 µg |
| Gelatin | 8~12 mg |
| Saccharose | 80~120 mg |
| KCl | 8~12 mg |
| Sodium glutamate | 8~12 mg |
| $H_2O$ for injection | q.s. to 1 ml |
| pH | 6.0~7.5 |

(2) Providing a stock solution of HBsAg, wherein 1 mL stock solution of HBsAg is consisted of the following components:

| | |
|---|---|
| HBsAg | 50~200 µg |
| NaCl | 8~9 mg |
| $H_2O$ for injection | q.s. to 1 ml |

(3) Mixing the stock solution of BCG obtained in step (1) with the stock solution of HBsAg obtained in step (2) in a proportion of 1:1 (v/v) to prepare a semi-finished product of the HBsAg-BCG combined vaccine, (4) Distributing the semi-finished product of the HBsAg-BCG combined vaccine obtained in step (3) into vials, 0.2 ml per vial, (5) Lyophilizing the vials obtained in step (4) to prepare a finished product of the HBsAg-BCG combined vaccine, i.e. a lyophilized formulation, wherein the vials are precooled in a drying oven for 3-4 hours, frozen for 7-8 hours, dried in vacuum for 8-10 hours at a gradually increasing temperature, and dried in vacuum for 7-8 hours at a constant temperature, the overall time amounting to 25-30 hours.

Inoculation Dosage and Injection Site of the HBsAg-BCG Combined Vaccine

Intracutaneous injection of HBsAg-BCG combined vaccine at a low dosage: 5 µg HBsAg and 80-120 µg BCG is contained in each of 0.2 ml vials, and dissolved in 0.2 ml of water for injection. 0.1 ml of the obtained solution is intracutaneously injected into the middle-lower outside part of deltoid muscle of the upper arm.

Intracutaneous injection of HBsAg-BCG combined vaccine at a moderate dosage: 10 µg HBsAg and 80-120 µg BCG is contained in each of 0.2 ml vials, and dissolved in 0.2 ml of water for injection. 0.1 ml of the obtained solution is intracutaneously injected into the middle-lower outside part of deltoid muscle of the upper arm.

Intracutaneous injection of HBsAg-BCG combined vaccine at a high dosage: 20 µg HBsAg and 80-120 µg BCG is contained in each of 0.2 ml vials, and dissolved in 0.2 ml of water for injection. 0.1 ml of the obtained solution is intracutaneously injected into the middle-lower outside part of deltoid muscle of the upper arm.

The Comparison of Immunogenicity Between the HBsAg-BCG Combined Vaccine for Intracutaneous Injection and Univalent BCG Vaccine The experiment group was inoculated with HBsAg-BCG combined vaccines at above three different dosages, while the control group was inoculated with BCG at the same dosages. Four guinea pigs were inoculated for each group. After five weeks, 10 IU/0.2 ml of Purified Protein Derivative of Tuberculin (PPD) was used to perform intracutaneous test. The diameter of scleroma for local reaction was determined after 24-72 hours. The experiment was conducted in triplicate.

At 24 hours after the PPD intracutaneous test, the results were obtained and used to compare the experiment group and the corresponding control group (see Table 1). The statistical analysis of the results showed no significant difference between the HBsAg-BCG combined vaccine and the univalent BCG vaccine (t test, $p>0.05$). Thus, the BCG vaccine contained in the HBsAg-BCG combined vaccine retained its immunogenicity.

The immunization procedure of the experiment groups was same as that of control group. Three experiment groups were intracutaneously injected with the HBsAg-BCG combined vaccines at three different dosages, i.e. 2.5 μg (5 μg/0.2 ml/vial), 5 μg (10 μg/0.2 ml/vial) and 10 μg (20 μg/0.2 ml/vial) of HBsAg, respectively. The second and the third injections are same as the control group. Each Guinea pig was intraperitoneally injected with 10 μg/1 ml of univalent HBsAg vaccine for intracutaneous injection.

Blood samples were taken one month after each immunization and the antibody titer of serum was measured by ELISA method. The results were shown in Tables 2-4.

TABLE 2

Comparison of immunology effects between experiment group (2.5 μg, HBsAg) and control group (10 μg, HBsAg)

| Group | Geometric mean of antibody titer of serum (GMT ± s) | | |
|---|---|---|---|
| | S1 | S2 | S3 |
| Experiment group | 66 ± 0.13 (n = 9) | 9164 ± 0.47 (n = 10) | 17811 ± 0.33 (n = 9) |
| Control group | 151 ± 0.25 (n = 8) P > 0.05 | 5596 ± 0.43 (n = 10) P > 0.05 | 11271 ± 0.23 (n = 11) P > 0.05 |

*S1, S2 and S3 are the geometric means of the antibody titer of serums after the first, second and third injection, respectively.

TABLE 1

Comparison of PPD test results of experiment group and control group

| Group | Vaccine | Dosage of HBsAg (μg/0.2 ml) | Diameter of scleroma (mm) | | | | x ± s | p |
|---|---|---|---|---|---|---|---|---|
| Experiment group 1-1 | HBsAg-BCG | 5 | 8 | 12 | 14 | 8.5 | 10.6 ± 2.86 | p > 0.05 |
| Experiment group 1-2 | HBsAg-BCG | 10 | 11.5 | 9 | 13 | 8.5 | 10.5 ± 2.12 | |
| Experiment group 1-3 | HBsAg-BCG | 20 | 10 | 11 | 10.5 | 7 | 9.6 ± 1.79 | |
| Control group 1 | BCG | 0 | 10.5 | 9.5 | 9 | 13 | 10.5 ± 1.77 | |
| Experiment group 2-1 | HBsAg-BCG | 5 | 11.5 | 10 | 12 | 9 | 10.6 ± 1.37 | p > 0.05 |
| Experiment group 2-2 | HBsAg-BCG | 10 | 14 | 8 | 12 | 8.5 | 10.1 ± 2.71 | |
| Experiment group 2-3 | HBsAg-BCG | 20 | 10.5 | 14 | 11 | 9.5 | 11.2 ± 1.93 | |
| Control group 2 | BCG | 0 | 14 | 12 | 10.5 | 8 | 11.1 ± 2.52 | |
| Experiment group 3-1 | HBsAg-BCG | 5 | 9 | 8.5 | 7 | 10 | 8.6 ± 1.25 | p > 0.05 |
| Experiment group 3-2 | HBsAg-BCG | 10 | 6.5 | 8 | 12 | 9 | 8.8 ± 2.32 | |
| Experiment group 3-3 | HBsAg-BCG | 20 | 7.5 | 8.5 | 10 | 8 | 8.5 ± 1.08 | |
| Control group 3 | BCG | 0 | 7.5 | 6.5 | 10 | 11.5 | 8.8 ± 2.28 | |

The Comparison of Immunogenicity Between the HBsAg-BCG Combined Vaccine for Intracutaneous Injection and Univalent HBsAg Vaccine for Intracutaneous Injection The conventional univalent HBsAg for intracutaneous injection contains aluminium adjuvant and a preservative. In contrast, the HBsAg-BCG combined vaccine prepared according to the present invention contains BCG vaccine as an immunogen as well as an adjuvant for the HBsAg. The following study was conducted to investigate the influence of BCG vaccine on the immunogenicity of HBsAg.

The control group was intraperitoneally inoculated with HBsAg vaccine for intracutaneous injection in three consecutive months, 10 μg/1 ml for each Guinea pig at each time.

TABLE 3

Comparison of immunology effects between experiment group
(5 μg, HBsAg) and control group (10 μg, HBsAg)

| Group | Geometric mean of antibody titer of serum (GMT ± s) | | |
|---|---|---|---|
| | S1 | S2 | S3 |
| Experiment group | 74 ± 0.22 (n = 8) | 10950 ± 0.38 (n = 9) | 16882 ± 0.42 (n = 8) |
| Control group | 151 ± 0.25 (n = 8) | 5596 ± 0.43 (n = 10) | 11271 ± 0.23 (n = 11) |
| | $P > 0.05$ | $P > 0.05$ | $P > 0.05$ |

TABLE 4

Comparison of immunology effects between experiment group
(10 μg, HBsAg) and control group (10 μg, HBsAg)

| Group | Geometric mean of antibody titer of serum (GMT ± s) | | |
|---|---|---|---|
| | S1 | S2 | S3 |
| Experiment group | 85 ± 0.32 (n = 9) | 12561 ± 0.59 (n = 10) | 18756 ± 0.43 (n = 9) |
| Control group | 151 ± 0.25 (n = 8) | 5596 ± 0.43 (n = 10) | 11271 ± 0.23 (n = 11) |
| | $P > 0.05$ | $P > 0.05$ | $P > 0.05$ |

As shown in Tables 2, 3 and 4, after the first injection of the HBsAg-BCG combined vaccine for intracutaneous injection at above three dosages (2.5 μg, 5 μg and 10 μg), the geometric means of antibody titer of serum in all of above cases are lower than that in the corresponding control group, wherein 10 μg of univalent HBsAg vaccine was inoculated intraperitoneally in the control group. After the second and the third injections, however, the antibody titers of the experiment groups (the HBsAg-BCG combined vaccine group) showed a rapid increase and were higher than that of the control group. The above results demonstrated that the BCG vaccine in the HBsAg-BCG combined vaccine not only did not have adverse effect on the overall immunogenicity of the HBsAg vaccine, but also had an effect of immunological enhancement.

The Effect of Dosage of the HBsAg-BCG Combined Vaccine for Intracutaneous Injection on the Immunogenicity of HBsAg Three different kinds of HBsAg-BCG combined vaccines were prepared according to the method of the present invention, wherein the contents of the HBsAg were 5 μg/0.2 ml/vial, 10 μg/0.2 ml/vial and 20 μg/0.2 ml/vial in the three HBsAg-BCG combined vaccines, respectively. The content of BCG in the three HBsAg-BCG combined vaccines was 80-120 μg/0.2 ml/vial. The above three HBsAg-BCG combined vaccines were dissolved in 0.2 ml of water for injection and 0.1 ml of obtained solution was used for intracutaneous injection. Guinea pigs which were negative in the "PPD intracutaneous test" were inoculated intraperitoneally with the HBsAg-BCG combined vaccines, 10 μg/1 ml for each guinea pig. The antibody titer in serum was measured by ELISA method. As seen from the results in Table 5, the immunization effects of the HBsAg-BCG combined vaccines at three different dosages of inoculation were similar and there was no significant difference among the groups in terms of geometric mean of antibody titer.

TABLE 5

Comparison of immunization effects of the HBsAg-BCG combined
vaccines at three different dosages of inoculation

| Dosage of inoculation | Geometric mean of antibody titer of serum (GMT ± s) | | |
|---|---|---|---|
| | S1 | S2 | S3 |
| 10 μg | 85 ± 0.32 (n = 9) | 12561 ± 0.59 (n = 10) | 18765 ± 0.43 (n = 9) |
| 5 μg | 74 ± 0.22 (n = 8) | 10950 ± 0.38 (n = 9) | 16882 ± 0.42 (n = 8) |
| 2.5 μg | 66 ± 0.13 (n = 90) | 9164 ± 0.47 (n = 10) | 17811 ± 0.33 (n = 9) |
| | $P > 0.05$ | $P > 0.05$ | $P > 0.05$ |

Safety Test of the HBsAg-BCG Combined Vaccine for Intracutaneous Injection

The HBsAg-BCG combined vaccine and the stock solution of BCG used for its preparation were dissolved in water for injection and inoculated intraperitoneally into guinea pigs of the same sex, wherein the guinea pigs were negative in "PPD intracutaneous test" and 300-400 g in weight. The guinea pigs were divided into two groups, experiment group and control group. The experiment group was inoculated intracutaneously with the HBsAg-BCG combined vaccine (HBsAg 0.5 mg, BCG 2.5 mg/1 ml, corresponding to a dosage for 50 persons), while the control group was inoculated intracutaneously with BCG vaccine (BCG 2.5 mg/i ml, corresponding to a dosage for 50 persons). The body weights of guinea pigs were measured every two weeks. After observation for six weeks, the guinea pigs were dissected for examination.

The safety test was repeated for three times. All of the guinea pigs in the experiment group (HBsAg-BCG combined vaccine group) showed an increase in body weight and no tuberculosis was found. In addition, the anatomic observation demonstrated that the viscera such as liver, spleen, lung, kidney, epiploon and mesentery in the experiment group and those in the control group (BCG group) showed no difference.

One advantage of the present invention is that with one injection of the HBsAg-BCG combined vaccine for intracutaneous injection according to the present invention, the neonates can acquire the immunities to Hepatitis B as well as Tuberculosis. The immunization effect of one injection of HBsAg-BCG combined vaccine is equal to or better than that of original two injections of univalent vaccines (HBsAg and BCG vaccines).

Another advantage of the present invention is the improved safety of the HBsAg-BCG combined vaccine compared with the original univalent HBsAg vaccine. The HBsAg-BCG combined vaccine according to present invention is not a simple mixture of the HBsAg and BCG vaccines, but a natural combination of HBsAg and BCG vaccines. The aluminum adjuvant, formaldehyde and merthiolate conventionally used in HBsAg vaccine are removed and safety is improved. The BCG in the HBsAg-BCG combined vaccine not only acts as a strong immunological adjuvant, but also enhances humoral immunity as well as cellular immunity. Thus, the immunization effect of the HBsAg-BCG combined vaccine is better than the univalent HBsAg vaccine. The distinctiveness of BCG vaccine requires an intracutaneous inoculation. Therefore, intracutaneous injection is selected as the only inoculation pathway of the HBsAg-BCG combined vaccine. Generally, the intracutaneous injection is also the most efficient pathway for stimulating the immune response of body. The immunization effect of intracutaneous inoculation at low dosage is equal to or even better than that of non-intracutaneous inoculation at high dosage.

A still another advantage of the present invention is that the HBsAg-BCG combined vaccine can be formulated in a lyophilized form while the conventional HBsAg vaccine is in a liquid form, and the heat stability of HBsAg is improved. Commonly, the effectiveness of HBsAg vaccine in liquid form decreases obviously or even by 50% after 15 days at 37° C. Because of the presence of the cryoprotective agent in the HBsAg-BCG combined vaccine, the heat stability of HBsAg is improved. As shown by ELISA results (see Table 6), the effectiveness of HBsAg in the HBsAg-BCG combined vaccine was well maintained even after 30 days at 37° C.

TABLE 6

ELISA results of the HBsAg-BCG combined vaccine after 30 days at 37° C.

| Groups | Dosage of HBsAg (μg/0.2 ml) | Original titer of HBsAg | Final titer of HBsAg after 30 days at 37° C. |
|---|---|---|---|
| 1 | 5 | 6.72 | 6.32 |
| 2 | 10 | 10.83 | 11.51 |
| 3 | 20 | 19.65 | 21.33 |

BEST MODE FOR CARRYING OUT THE PRESENT INVENTION

EXAMPLE 1

Preparation of Stock Solution of HBsAg for Intracutaneous Injection

According to the "Requirements for Hepatitis B Vaccine Made by Recombinant DNA Techniques in CHO cell" of "Chinese Requirements of Biologics" (Edition 2000), CHO-C28 cell (the passage number of the cell should not exceed 30), which contains a gene encoding HBsAg, was grown, passaged and inoculated into a 15 L roller bottle or bioreactor. After incubation at 37° C., the culture was collected and purified HBsAg was obtained with a purity of over 95%. After sterilization by filtration, the HBsAg was diluted with normal saline to 50-200 μg/ml.

EXAMPLE 2

Preparation of Stock Solution of BCG

According to the "Requirements for BCG vaccine for intracutaneous injection" of the "Chinese Requirements of Biologics" (Edition 2000), bacterial strain was cultured and grown in Souton potato solid and liquid media. Mycoderm was collected, pressed to dry, triturated at low temperature and diluted with a protectant to a concentration of 0.8-1.2 mg/ml.

EXAMPLE 3

Preparation of Cryoprotective Agent Useful for the HBsAg-BCG Combined Vaccine

The cryoprotective agent useful for the HBsAg-BCG combined vaccine was formulated as follows:

| Components | content (shown as percentage by weight) |
|---|---|
| Gelatin | 0.8~1.0 g |
| Saccharose | 8~12 g |
| KCl | 0.8~1.2 g |

-continued

| Components | content (shown as percentage by weight) |
|---|---|
| Sodium Glutamate | 0.8~1.2 g |
| Water for injection | q.s. to 100 ml |
| pH | 6.0~7.5 |

EXAMPLE 4

Preparation of Semi-Finished Product of the HBsAg-BCG Combined Vaccine for Intracutaneous Injection The semi-finished product of the HBsAg-BCG combined vaccine for intracutaneous injection was formulated as follows:

| Components | content (per ml) |
|---|---|
| HbsAg | 25-100 μg |
| BCG | 400-600 μg |
| Gelatin | 4-6 mg |
| Saccharose | 40-60 mg |
| KCl | 4-6 mg |
| Sodium Glutamate | 4-6 mg |
| Water for injection | q.s. to 1 ml |
| pH | 6.0~7.5 |

EXAMPLE 5

Preparation of the Finished Product of the HBsAg-BCG Combined Vaccine for Intracutaneous Injection The semi-finished product of the HBsAg-BCG combined vaccine obtained in Example 4 was distributed into vials, 0.2 ml per vial. The vials obtained was freeze dried to prepare a finished product of the HBsAg-BCG combined vaccine, i.e. a lyophilized formulation, wherein the vials were precooled in a drying oven at −30° C. to −40° C. for 3-4 hours, frozen for 7-8 hours to a temperature of −30° C. to −40° C., dried in vacuum for 8-10 hours at a gradually increasing temperature from −40° C. to 38° C., and dried in vacuum for 7-8 hours at a constant temperature of 33-38° C., the overall time amounting to 25-30 hours. The finished product of the HBsAg-BCG combined vaccine after lyophilization was a white loose material with a water content of ≦3% (g/g).

What is claimed is:

1. A HBsAg-BCG combined vaccine for intracutaneous injection, consisting of the following components (0.2 ml per vial):

| HBsAg (Hepatitis B virus surface Antigen) | 5 μg~20 μg |
|---|---|
| BCG (Bacille Calmette-Guérin) | 80 μg~120 μg |
| Gelatin | 0.8~1.0 mg |
| Saccharose | 8~12 mg |
| KCl | 0.8~1.2 mg |
| Sodium glutamate | 0.8~1.2 mg |
| NaCl | 0.8~0.9 mg |
| $H_2O$ for injection | q.s. |
| pH | 6.0~7.5. |

2. A method for the preparation of HBsAg-BCG combined vaccine according to claim 1, including the following steps:

(1) providing a stock solution of BCG, wherein 1 mL stock solution of BCG is consisted of the following components:

| | |
|---|---|
| BCG | 800~1200 μg |
| Gelatin | 8~12 mg |
| Saccharose | 80~120 mg |
| KCl | 8~12 mg |
| Sodium glutamate | 8~12 mg |
| $H_2O$ for injection | q.s. to 1 ml |
| pH | 6.0~7.5 |

(2) providing a stock solution of HBsAg, wherein 1 mL stock solution of HBsAg is consisted of the following components:

| | |
|---|---|
| HBsAg | 50~200 μg |
| NaCl | 8~9 mg |
| $H_2O$ for injection | q.s. to 1 ml |
| pH | 6.0~7.5 |

(3) mixing the stock solution of BCG obtained in step (1) with the stock solution of HBsAg obtained in step (2) in a proportion of 1:1 (v/v) to prepare a semi-finished product of the HBsAg-BCG combined vaccine, (4) distributing the semi-finished product of the HBsAg-BCG combined vaccine obtained in step (3) into vials, 0.2 ml per vial, (5) lyophilizing the vials obtained in step (4) to prepare a finished product of the HBsAg-BCG combined vaccine, i.e. a lyophilized formulation, wherein the vials are pre-cooled in a drying oven at $-40°$ for 3-4 hours, frozen at $-40°$ for 7-8 hours, dried in vacuum for 8-10 hours at a gradually increasing temperature, and dried in vacuum for 7-8 hours at a constant temperature of 30-35° C., the overall time amounting to 25-30 hours.

3. The HBsAg-BCG combined vaccine according to claim 1, which is in a lyophilized form.

* * * * *

UNITED STATES PATENT AND TRADEMARK OFFICE
CERTIFICATE OF CORRECTION

PATENT NO. : 7,579,003 B2  Page 1 of 1
APPLICATION NO. : 10/559471
DATED : August 25, 2009
INVENTOR(S) : Jin et al.

It is certified that error appears in the above-identified patent and that said Letters Patent is hereby corrected as shown below:

At Column 10, line 14, in Claim 2, after "40°" please add --C--.

At Column 10, line 15, in Claim 2, after "40°" please add --C--.

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,579,003 B2 Page 1 of 1
APPLICATION NO. : 10/559471
DATED : August 25, 2009
INVENTOR(S) : Jin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this

Fourteenth Day of September, 2010

David J. Kappos
*Director of the United States Patent and Trademark Office*